United States Patent
Tiitta et al.

(10) Patent No.: US 7,329,788 B2
(45) Date of Patent: Feb. 12, 2008

(54) PROCESS FOR PRODUCING GASOLINE COMPONENTS

(75) Inventors: Marja Tiitta, Porvoo (FI); Elina Harlin, Vantaa (FI); Antti Pyhälahti, Helsinki (FI)

(73) Assignee: Neste Oil Oyj, Espoo (FI)

( * ) Notice: Subject to any disclaimer, the term of this patent is extended or adjusted under 35 U.S.C. 154(b) by 677 days.

(21) Appl. No.: 10/740,457

(22) Filed: Dec. 22, 2003

(65) Prior Publication Data

US 2005/0137435 A1 Jun. 23, 2005

(51) Int. Cl.
*C07C 2/06* (2006.01)
*C07C 5/25* (2006.01)

(52) U.S. Cl. .............. 585/332; 585/329; 585/377; 585/327; 585/510; 585/518; 585/664

(58) Field of Classification Search .............. 585/644, 585/508
See application file for complete search history.

(56) References Cited

U.S. PATENT DOCUMENTS

| | | | |
|---|---|---|---|
| 3,325,465 A | 6/1967 | Jones et al. | |
| 6,008,426 A | 12/1999 | Oorschot et al. | |
| 6,518,473 B2 * | 2/2003 | Miller et al. | 585/517 |
| 6,613,108 B1 | 9/2003 | Aittamaa et al. | |
| 2002/0128530 A1 | 9/2002 | Miller et al. | |
| 2004/0176655 A1 | 9/2004 | Ayoub et al. | |

FOREIGN PATENT DOCUMENTS

| | | |
|---|---|---|
| DE | 3542171 A1 | 6/1987 |
| EP | 0224220 B1 | 2/1989 |
| EP | 0994088 A1 | 4/2000 |
| FR | 2515171 | 10/1981 |
| GB | 595827 | 12/1947 |
| RU | 2165913 C2 | 4/2001 |
| WO | 00/23402 A1 | 4/2000 |
| WO | WO 01/46095 A1 | 6/2001 |
| WO | 2004/072001 A1 | 8/2004 |
| WO | 2004/072006 A1 | 8/2004 |
| WO | 2004/080935 A1 | 9/2004 |

OTHER PUBLICATIONS

ABSTRACT—DE3542171/EP0335330, Jun. 1987.
ABSTRACT—FR-2515171A, Apr. 1983.

* cited by examiner

*Primary Examiner*—Tam M. Nguyen
(74) *Attorney, Agent, or Firm*—Birch, Stewart, Kolasch & Birch, LLP (57) ABSTRACT

Process for producing gasoline components. The process comprises feeding a fresh olefinic hydrocarbon feedstock to a reaction zone, in which its structure is first isomerized. The isomerized hydrocarbon is drawn out of the first reaction zone and conducted to a second reaction zone, where the isomerized hydrocarbon is dimerized. The dimerized reaction product is drawn out of the second reaction zone and separated from the flow in a separation zone. Because there are more isoolefins present in the dimerization unit feed, more isoolefin dimers useful as fuel components can be produced.

31 Claims, 4 Drawing Sheets

PROCESS FOR PRODUCING GASOLINE COMPONENTS

BACKGROUND OF THE INVENTION

1. Field of the Invention

The present invention relates to selective production of $C_6$-$C_{12}$ hydrocarbons useful as automotive fuel components. In particular, the present invention concerns a process for treating a fresh olefinic hydrocarbon feedstock in a reactor assembly comprising at least two reaction zones arranged in a cascade for converting lower olefins of the olefinic feedstock into gasoline grade dimerized components.

2. Description of Related Art

In oil refining processes, several streams containing light olefins emanate from various sources. Light n-olefins can be converted to more valuable hydrocarbon-based gasoline components or to a feedstock for gasoline components by means of several processes, namely, isomerization, etherification, dimerization and alkylation. Thus, in many modern refineries, streams containing these components are treated so that first the $C_4$-$C_7$ isoolefins (e.g. isobutene, 1-methyl-1-butene, 2-methyl-2-butene, 1-methyl-1-pentene, 2-methyl-2-pentene and 2-ethyl-1-butene) are converted to ethers and, then, the remaining raffinate stream is conducted to an alkylation unit, where the remaining—mainly linear—olefins are reacted with isoparaffins. These streams are utilized, for example, in the production of gasoline for automotive engines.

A reaction step where isoolefins are removed before alkylation has a positive effect on the overall operation, because the tertiary ethers resulting from the reactions of the isoolefins are excellent gasoline components. Moreover, isoolefins tend to be too reactive in alkylation and they therefore react readily to yield unwanted side products. Finally, the total amount of olefins present in the feed stream tends to be higher than the amount of available isoparaffins and any alkylate production is limited by the amount of isoparaffins in the feed. When isoolefins are consumed before alkylation, the total amount of gasoline components increases and the quality of the combined product is improved.

This processing chain can be improved, if the feed is totally or partially treated in a skeletal isomerization unit before the etherification. Then, the yield of ethers can be increased because linear olefins are converted to isoolefins and the ratio of isoparaffins to olefins in the remaining raffinate stream is closer to optimal because a larger proportion of the olefins reacts already before the alkylation unit. With sufficient recycle of linear olefins, it is even possible to convert most of the linear olefins to isoolefins. There are several publications concerning the combination of etherification and skeletal isomerization.

However, in recent times, etherification has become questionable because of the water pollution caused by MTBE released from leaking gasoline storage tanks. There is a need for a process that would maximize the yield of useful fuel components from a light hydrocarbon feed without resorting to etherification.

An alternative to etherification of light isoolefins is to use them in dimerization, as disclosed in U.S. Pat. Nos. 3,325,465 and 6,613,108, DE Patent No. 3,542,171 and International Patent Application WO 01/46095.

A number of processes involving both dimerization and isomerization steps are also known in the art.

Thus, FR 2525171 discloses a combination of oligomerization and skeletal isomerisation of isobutene. The oligomerization is first performed and the oligomerate is separated. Then, butanes are separated by extractive distillation and the remaining butenes are skeletal-isomerized. The isomerized butene is circulated back to oligomerization. The process requires the use of extractive distillation for the separation of butanes. GB 595827 discloses a system with a sequence of oligomerization-isomerization-oligomerization and dehydrogenation for the production of high-grade motor or aviation fuels. RU 2165913 discloses a process for converting n-alkanes into isoalkenes. The essential components of the system are dehydrogenation and skeletal isomerization thereafter. Dehydrogenation is an expensive process and requires a costly investment in the process design and equipment. The process is carried out in the presence of polar compounds that later on need to be separated from the reaction product. This also is costly.

None of the above processes provides an integral process for producing from a fresh olefinic feedstock gasoline grade components, which meet present standards and requirements.

SUMMARY OF THE INVENTION

It is an object of the present invention to eliminate problems of prior art and to provide a novel process for the production of gasoline components from an olefinic $C_3$-$C_7$ hydrocarbon stream. In particular, it is an object of the invention to provide a process for dimerizing olefinic hydrocarbons.

It is another object of the invention to provide a process for converting a fresh olefinic hydrocarbon feedstock, mainly containing linear and branched $C_3$-$C_7$ olefins, into a hydrocarbon product comprising gasoline grade dimerized components.

The invention is based on the idea of first modifying the isomeric structure of a fresh olefinic feedstock and then dimerizing the modified olefins along with other isoolefins and reactive olefins (including linear and branched olefins) already present in the feed. According to the invention, the olefinic feedstock is contacted with an isomerization catalyst in order to obtain a product with a modified isomeric structure. The product, which comprises compounds having a modified isomeric structure, is then contacted with a dimerization catalyst in order to dimerize the isoolefins and, as will be explained below, to codimerize linear and isomerized olefins to the corresponding dimers. The catalysts used in isomerization and dimerization may be the same or different.

The conditions of the process are selected so as to favor isomerization of olefins in the first reaction zone and selective dimerization in the second reaction zone.

Although recycling of the unreacted olefins is allowed and effected, the fresh feed makes up a considerable portion of the feed into the isomerization reaction zone; preferably at least 20 mole-% of the feed comprises fresh olefins.

More specifically, the dimerization process according to the present invention is mainly characterized by what is stated in the characterizing part of claim 1.

The process for converting an olefinic hydrocarbon feed into a useful gasoline component is characterized by what is stated in the characterizing part of claim 29.

Considerable advantages are achieved by means of the present invention. The benefits are much more numerous than if skeletal isomerization were combined with etherification.

The first and obvious benefit is that because there are more isoolefins present in the dimerization unit feed, more isoolefin dimers can be produced. As already mentioned, isoolefin dimers are useful fuel components as such.

A less obvious, but in a large-scale operation very significant advantage is related to side products of the dimerization process. It should be noted that in normal refinery streams there is a large amount of linear olefins in addition to isoolefins. E.g. in a typical $C_4$ stream from a fluidized catalytic cracking unit (FCC) there is approximately 15% of isobutene and 45% of 1-butene, cis-2-butene and trans-2-butene. When such a stream is used as a feedstock for isoolefin dimerization, besides isoolefin dimers, a significant amount of codimers between isoolefin and linear olefins will be produced. E.g. in dimerization of the above-mentioned FCC $C_4$ stream, as much as up to 15 to 25% of the total dimer product may consist of said codimers. Thus, the amount and quality of these side products is very important for the process economy. Usually the codimers formed from isoolefin and 2-olefins are more branched and have thereby a higher octane number than codimers formed from 1-olefins. E.g. when isobutene and 1-butene form codimers, the typical products are methylheptenes and dimethylhexenes, whereas codimers formed from cis-2-butene and trans-2-butene with isobutene are mainly trimethylpentenes having essentially higher octane numbers. Thus, the present invention makes it possible to utilize even those linear olefins, which have not reacted during isomerisation, for the production of gasoline grade olefins after dimerization.

The invention also provides thermodynamical improvements of the process economy. In refinery streams normally the ratio of 1-olefins to the 2-olefins is significantly higher than the thermodynamic equilibrium value would be at ambient temperatures. Combining this fact with what is stated above of the quality of side products of the dimerization reaction, it would be beneficial to bring the composition of the linear olefin fraction nearer to the equilibrium. This can be achieved by means of the present invention.

Now, besides causing rearrangement of carbon atoms of the molecule, the skeletal isomerization gives rise to double bond isomerization, as well, thus allowing the ratio of 1-olefins to 2-olefins to change towards equilibrium, thus improving the overall product quality of the dimerization step.

Another surprising benefit results from the fact that the catalyst used in isoolefin dimerization must be considerably more active than in etherification. Thus, there is a danger of formation of unwanted side products, such as polymers. In dimerization the catalyst is more vulnerable to many catalyst poisons than in etherification. For example butadiene and certain basic nitrogen compounds form a significantly more serious threat than in case of etherification. When a skeletal isomerization step is performed before the dimerization step, these catalyst poisons do not pose a threat to the process. This is due to the fact that poisons are adsorbed or reacted on skeletal isomerization catalyst and can be removed by regeneration. When cleaner feeds are conducted to dimerization, the lifetime of the dimerization catalyst is significantly increased. This means savings in the running cost of the process.

Moreover, the heat integration between isomerization and dimerization is possible because dimerization reactors operate at temperatures sufficient for vaporizing the skeletal isomerization feed. This also means savings in process costs and an ease of operation and process design.

The invention is described in the following with the aid of a detailed description and working examples.

DETAILED DESCRIPTION OF THE INVENTION

The Overall Process

According to a first preferred embodiment of the invention, the fresh hydrocarbon feed containing linear olefins is first conducted to a first reaction zone that comprises a skeletal isomerization unit. The feed is contacted with a first catalyst in order to produce a hydrocarbon having a modified isomeric structure. The effluent of the first reaction zone, containing the hydrocarbons with a modified isomeric structure, is conducted to a second reaction zone that comprises a dimerization unit. The conditions in the second reaction zone are such that at least a part of the hydrocarbons are dimerized. The effluent from the second reaction zone is conducted to a separation zone. In this unit the produced dimers are separated and the remaining light hydrocarbons are partially recycled back to the first reaction zone to the skeletal isomerization. A part of the light hydrocarbons may be drawn out of the system. The conditions in the first and the second reaction zone and in the separation zone are essentially oxygenate-free, which means that the amount of polar compounds is less than 0.5 mole-% of the olefinic hydrocarbons fed into the reaction zone.

Figure 1:
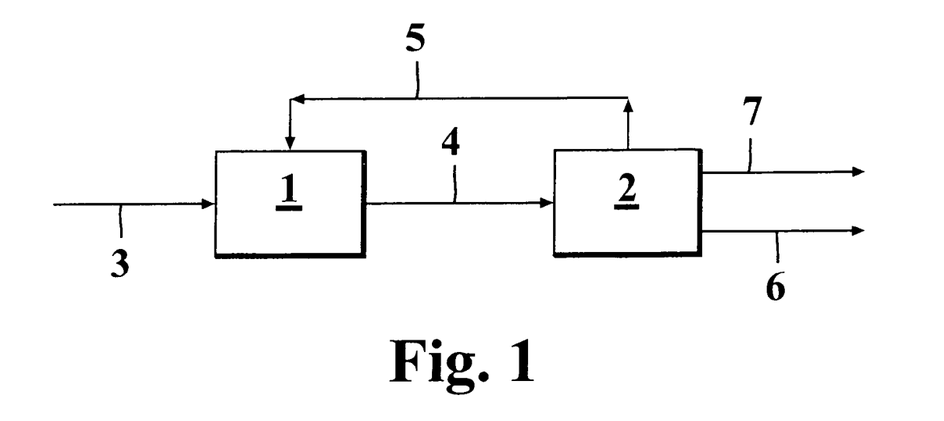
FIG. 1 depicts in a schematic fashion the process configuration of the basic technical solution of the invention, in which the fresh feed is fed to the first reaction zone and the effluent is conducted to the second reaction zone.

FIG. 1 presents an embodiment of the invention. In the arrangement of FIG. 1, the skeletal isomerization unit 1 treats all feed 3 entering the unit and thus the benefits concerning side products are utilized in maximal way. On the other hand, when skeletal isomerization unit is placed in recycle stream containing only a small amount of isoolefins, the skeletal isomerization works with maximum one pass conversion and the unit can be smaller because it treats only the recycle stream. This may be economical way of operation e.g., if goal is not to maximize the dimer yield but only to optimize the olefin/isoparaffin ratio in the raffinate stream 7 used as alkylation feed.

According to an embodiment, the fresh olefinic feedstock is a hydrocarbon mixture containing olefins. The feed comprises olefins at least 10 wt-%, preferably at least approximately 20 wt-%. The fresh olefinic feedstock comprises $C_3$-$C_{10}$ olefins, preferably $C_3$-$C_7$ olefins. According to a preferred embodiment of the invention, the fresh, olefinic feedstock comprises linear and branched $C_4$-olefins such as 1-butene, 2-butene or isobutene.

As already described, the olefins are selected from the group of propene, linear 1- or 2-butene, isobutene and linear or branched $C_5$-olefins. Alternatively, the feed can comprise a mixture of any or every of the olefins listed above. Typically, the feed comprises $C_4$-olefins or $C_5$-olefins. It is clear that both $C_4$- and $C_5$-olefins can be present in the feed, whereby a great variety of products is produced. The composition of the product flow is discussed later.

The fresh, olefinic feed may be selected from the group containing $C_4$-fractions of FCC, TCC, DCC and RCC or from the $C_4$-fraction after the removal of butadiene. The product from the FCC is typically composed of 10-50, in particular 10-30 wt-% isobutene, 20-70 wt-% 1- and 2-butene and approximately 5-40 wt-% butane. As an example of a typical FCC-mixture, the following can be presented: approximately 17 wt-% isobutene, approximately 17 wt-% 1-butene, approximately 33 wt-% 2-butene and approximately 33 wt-% butane, and others.

Also hydrocarbons prepared from chemicals can be used as the fresh, olefinic feed.

A "reaction zone" comprises at least one, typically two or three, reactor(s). The reactors may be connected in series or in parallel, including any combination of these.

The reactor can be any continuous type reactor, in which a solid catalyst can be placed and that is capable of handling liquid or gaseous reagents. Advantageously, the reactor is a simple tubular reactor, a packed bed reactor or a fluidized bed reactor. The reactor can be a tubular reactor with multiple pipes, wherein the pipes are filled with catalyst. Other possibilities include a reactive distillation unit with side reactors. The operating pressure and the temperature of the reactors depend on the type of the reactor and on the composition of the feed. In order to be able to regenerate the catalyst during reactor operation, it is often advantageous to use at least two reactors that can be regenerated in turn. Another advantageous mode of operation is to use a reactor, in which the catalyst can be regenerated continuously.

According to an embodiment of the invention, the first reaction zone comprises a continuous-working fluidized-bed reactor or circulating-bed reactor system, wherein the olefin feed is contacted with catalyst particles in a fluidized state. The conditions in the first reaction zone are selected as to favor isomerization. Advantageously, the reaction is performed in gas phase. The temperature in the first reaction zone is typically 25-500° C., preferably 100-400° C. and the pressure is 0.1 to 10 bar, preferably the pressure is so high that the effluent can be condensed at ambient or slightly above ambient temperature. According to another embodiment, the first reaction zone is a fixed bed reactor.

According to the invention, the first catalyst is an isomerization catalyst. Such catalysts include catalysts having acid sites. These catalysts are e.g. the group of zeolites, SAPO, amorphous aluminum silicate or aluminum oxide catalyst. According to a preferred embodiment, the zeolite is selected from the group consisting of synthetic and natural zeolites containing about 0.1 to 5 wt-%, preferably about 0.3 to 3 wt-%, in particular about 0.5 to 2 wt-%, aluminium. The zeolite is selected from the group consisting of medium pore zeolites like TON, MTT and ferrierite and ion-exchanged zeolites prepared therefrom. Such ion-exchanged zeolites may contain counter-ions selected from the group of alkali metal and alkaline earth metal ions, such as sodium, potassium, calcium and magnesium. However, the invention is not limited to the above-named catalyst grades alone, but rather, all such catalysts that catalyze the isomerization reactions of olefins are suited for use according to the invention. The catalysts can be pre- or posttreated or modified with the methods known in the art.

"Effluent" contains the desired product of the reaction in the reaction zone. The first effluent comprises hydrocarbons having a modified isomeric structure. In this context, a modified isomeric structure means that a straight chain hydrocarbon is transformed to a hydrocarbon having at least one alkyl side chain. The hydrocarbons having a modified isomeric structure also comprise the product of double bond isomerization. The place of the double bond of the hydrocarbon is changed during the isomerization. The hydrocarbons having a modified isomeric structure also comprise mixtures of hydrocarbons having at least one alkyl side chain and products of double bond isomerization.

The second reaction zone comprises one or several reactors. Many reactors of a continuous type capable of housing a solid catalyst and a liquid reagent are suitable for the invention. Optionally the reactor may allow regeneration of the catalyst. The regeneration can be done during continuous process operation. Alternatively, two or several reactors can be used in parallel, this allows regenerating one reactor when other is being operated. If the catalysts used in the first and second reaction zones are same, the regeneration system can be combined.

The conditions in the second reaction zone are chosen as to favor: selective dimerization. The temperature of the reaction zone is typically 50-200° C., preferably 80-150° C. Advantageously, the reaction takes place in liquid phase.

According to the invention, an acid catalyst is used as the second catalyst. Those may be based e.g. on ion-exchange resin catalyst or zeolite catalyst. In these conditions, medium pore zeolites, like ZSM-5, ferrierite, ZSM-22 and ZSM-23, or ion-exchange resins, like Amberlyst 15, Amberlyst 35, IO42 and IO43, are active and selective.

According to a preferred embodiment, the zeolite is selected from the group consisting of synthetic and natural zeolites containing about 0.1 to 5 wt-%, preferably about 0.3 to 3 wt-%, in particular about 0.5 to 2 wt-%, aluminium. The zeolite is selected from the group consisting of ZSM-5, ZSM-22, ZSM-23, ferrierite and ion-exchanged zeolites prepared therefrom. Such ion-exchanged zeolites may contain counter-ions selected from the group of alkali metal and alkaline earth metal ions, such as sodium, potassium, calcium and magnesium.

However, the invention is not limited to the above-named catalyst grades alone, but rather, all such acid catalysts that catalyze dimerization reactions of olefins are suited for use according to the invention.

The second effluent comprises the dimerized reaction product. For example, the dimerized reaction product for a feed comprising (among other, less reactive compounds) both $C_4$- and $C_5$-isoolefins (in a ratio 45:55) includes trimethylpentenes 20-30 wt-%, in particular 25-28 wt-%, tetramethylpentenes and trimethylhexenes 20-30 wt-%, in particular 20-25 wt-%, tetramethylhexenes 4-8 wt-%, in particular 5-6 wt-%, and trimethylheptenes 2-5 wt-%, in particular 3-4 wt-%. The rest of the dimer product is less branched olefins.

According to an embodiment, a part of the first product, which is not recycled, is transferred to alkylation.

According to a preferred embodiment of the invention, the separation zone comprises a distillation column. The product flow from the reaction zone comprises light hydrocarbons remaining from the hydrocarbon feed, and oligomers formed in the reactor having a boiling point substantially higher than that of the feed. This makes separation by distillation simple.

According to an embodiment of our invention, the separation zone is preferably a distillation zone. The reactants are monomers and the product is a mixture of oligomers and thus they have significantly different boiling points making separation by distillation easy. Considering the ease of separation, a flash drum, evaporator, stripper, or fractionator and other distillation devices known in the art can be used.

According to another embodiment of the invention, the dimerized reaction product is hydrogenated. The dimer product can be treated in a subsequent hydrogenation step in order to convert the olefinic product partially or completely to a paraffinic hydrocarbon product. If the dimerization step is performed in the presence of oxygenate moderator, the hydrogenation step also helps to remove the possible oxygenate impurities from the product.

In the attached drawings the alternative embodiments of the invention are illustrated in detail. Of the references 1, 21, A designate an isomeration zone
2, 22, B designate a dimeration zone
C, D designate a separation step, and
Alk. designates alkylation.

The meanings of other notations become apparent from the specification which follows.

Figure 2:
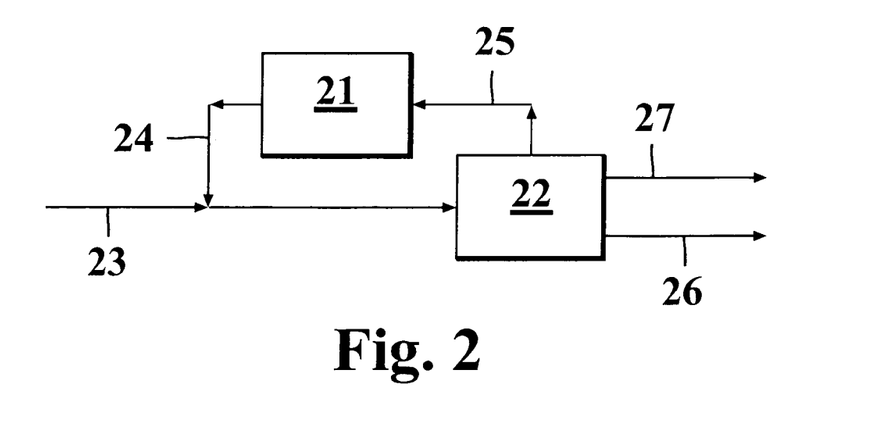
FIG. 2 depicts an embodiment in which the skeletal dimerization unit is placed in the recycle flow from the dimerization unit.

There are several possible ways to combine the skeletal isomerization and dimerization units to each other. FIGS. 1 and 2 present two examples of such combinations. In the embodiment of FIG. 1, the feed containing linear olefins (stream 3) is first conducted to a skeletal dimerization unit 1 and the effluent from this unit is conducted to the dimerization unit 2. In this unit the produced dimers are separated to stream 6 and the remaining light hydrocarbons are partially recycled back to the skeletal isomerization stage 1 via stream 5 and taken out from the system via stream 7.

In FIG. 2 the main parts of the arrangement are the same but the skeletal dimerization unit is placed in the recycle flow from the dimerization unit.

In the arrangement of FIG. 1, the skeletal isomerization unit 1 treats all feed 3 entering the unit and thus the benefits concerning side products are utilized in maximal way. On the other hand, in the arrangement of FIG. 2, when skeletal isomerization unit 22 is placed in recycle stream 25 containing only small amount of isoolefins, the skeletal isomerization works with maximum one pass conversion and the unit can be smaller because it treats only the recycle stream. This may be economical way of operation e.g., if goal is not to maximize the dimer yield but only to optimize the olefin/isoparaffin ratio in the raffinate stream 27 used as alkylation feed.

Figure 3:
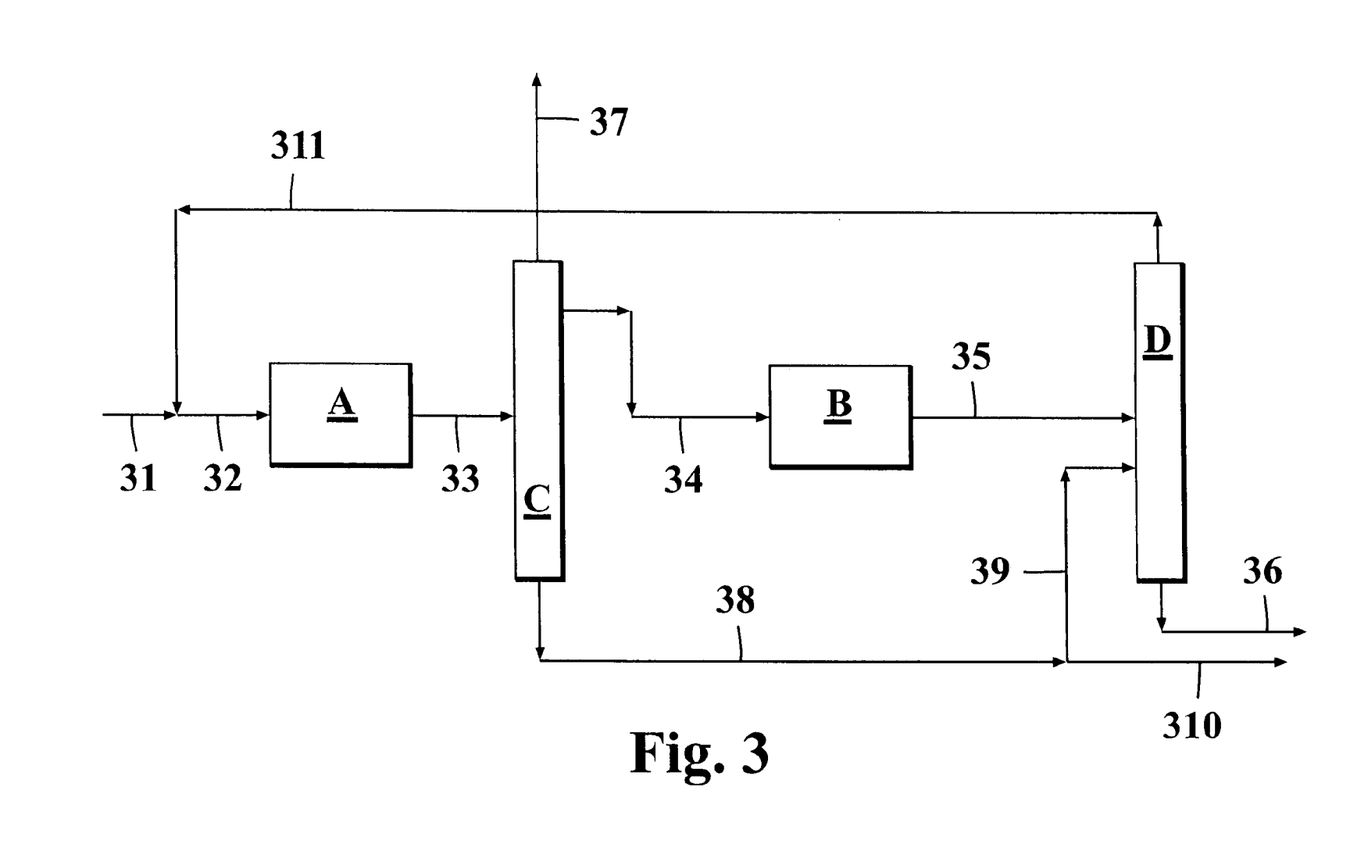
FIG. 3 depicts an embodiment in which a separation step is placed in between the isomerization and the dimerization and after the dimerization.

According to the embodiment presented in FIG. 3, a separation step C is placed in between the isomerization A and the dimerization B and another separation step D after the dimerization.

Figure 4:
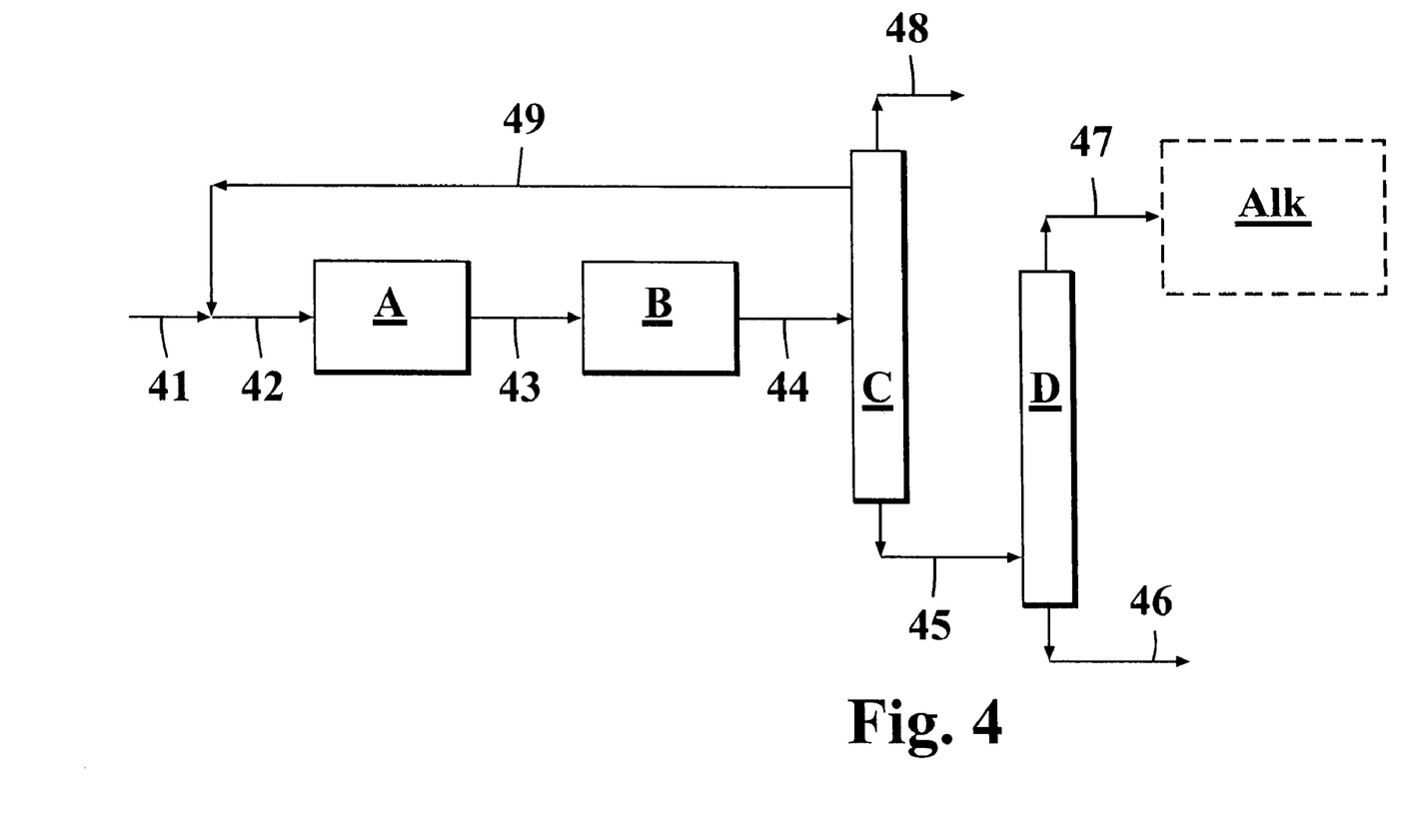
FIG. 4 depicts an embodiment in which there are two separation steps after dimerization and the separated light hydrocarbons are recycled back to the isomerization.

In the embodiment of FIG. 4, there are two separation steps C and D after dimerization B and the separated light hydrocarbons 49 are recycled back to the isomerization A. After the second separation step, the light hydrocarbons 47 are conducted into alkylation.

Figure 5:
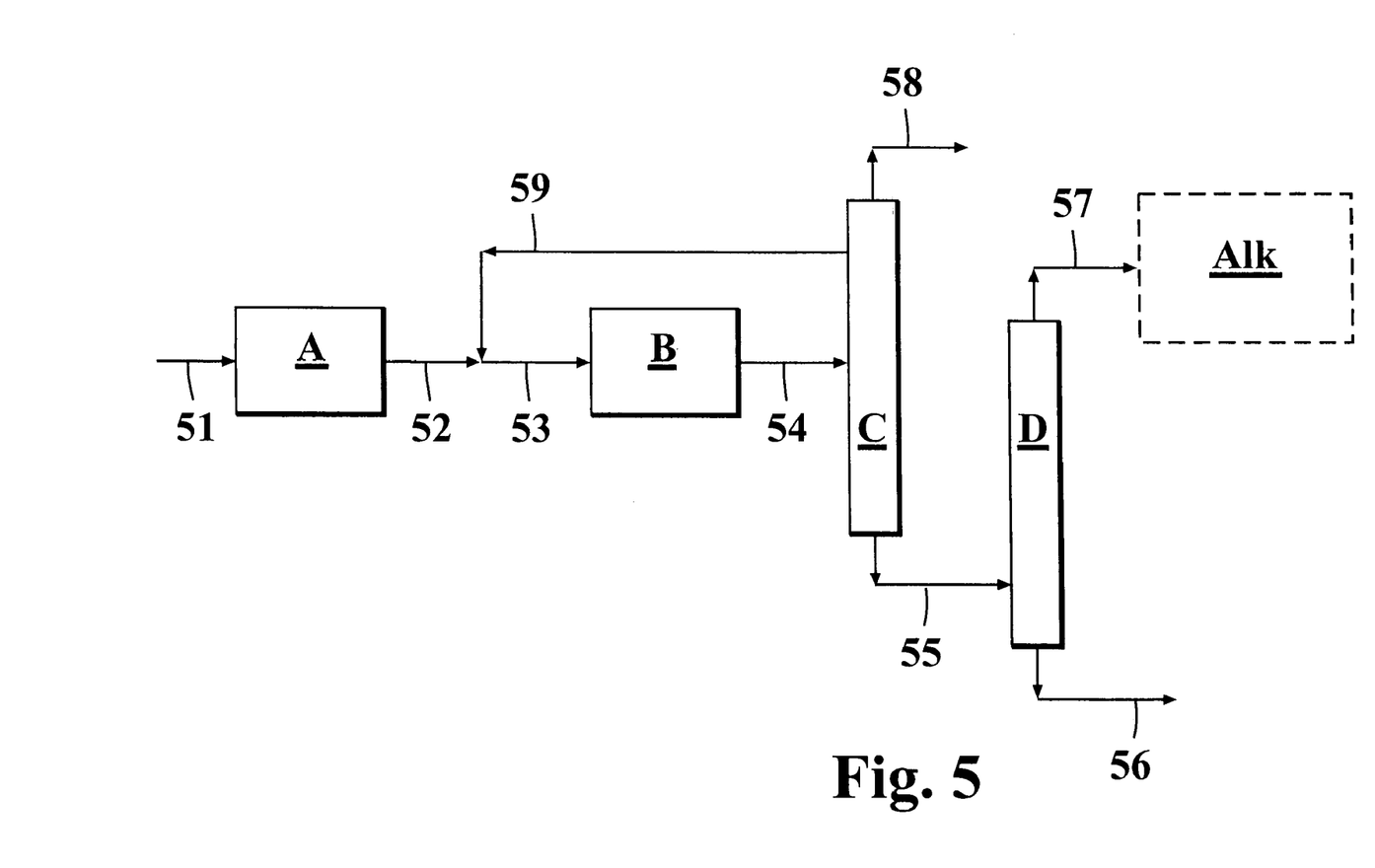
FIG. 5 depicts an embodiment in which there are two separation steps after dimerization and the separated light hydrocarbons are recycled back to dimerization.

FIG. 5 depicts an embodiment in which there are two separation steps C and D after dimerization B and the separated light hydrocarbons 59 are recycled back to dimerization B. After the second separation step D, the light hydrocarbons 57 are conducted into alkylation.

According to a preferred embodiment of the invention, essentially 50% of the $C_4$ hydrocarbons present in the feed are dimerized. In this embodiment, the remaining $C_4$ hydrocarbons are conducted into alkylation together with isobutene. According to this embodiment, 80-85% of the feed can be used as a gasoline component.

EXAMPLES

Three examples are presented in order to further illustrate the invention. The examples are all embodiments of the present invention.

These examples are only illustrations of possible process arrangements. Numerous other configurations are possible within the limits of the invention and even likely to occur when the process unit according to invention is accommodated to local conditions in a real-life plant.

The type of dimerization process will have an effect on the details of the whole process as well.

Example 1

The process configuration according to FIG. 3 was simulated for producing isoolefin dimers from a hydrocarbon feed containing $C_4$ hydrocarbons. The system has been optimized in order to get the amount of isobutane and butanes in flow leaving the unit to be equal.

Example 1 presents a system where the combination of skeletal isomerization and dimerization are used for producing an optimal feed for alkylation besides of producing dimer itself. In this case feed 31 is combined with the recycled $C_4$ fraction 311 and the combined stream 32 is conducted to the skeletal isomerization unit A. The resulting stream 33 is conducted to a $C_4$ splitter B, which is mainly intended to enrich the alkylation feed in respect of the higher boiling cis-2-butene and trans-2-butene, which are especially suited for alkylation feedstock. Moreover, from the top of this column is taken a $C_3$ stream 37 in order to prevent their accumulation to the recycle. This column requires significant reboiler duty at a relatively low temperature level. Thus the heat integration where the hot effluent of the skeletal isomerization is used for heating the reboiler of this column is easy to arrange and provides significant advantages. The isobutene rich stream is taken as a side draw 34 from the column B and conducted to the dimerization unit C. The effluent of this unit 35 is fed to the isooctene separation column D. This column separates the dimer product (stream 36) from the remaining $C_4$ fraction, which is recycled. The proportion of butenes converted to isooctene can be regulated by adjusting stream 39, because via this stream part of the linear butenes will return to the skeletal isomerization. This stream could be conducted directly to the feed of the skeletal dimerization unit as well. However in this case it is recycled via isooctene separation column D in order to remove the small amount of $C_5+$ components present in this stream.

The amounts and percentages of each component in each flow are presented in Table 1.

TABLE 1

| | Stream | | | | | | | | | | | |
|---|---|---|---|---|---|---|---|---|---|---|---|---|
| | 31 | | 32 | | 33 | | 37 | | 38 | | 39 | |
| C3 | 4.0 | 4.0% | 4.0 | 0.8% | 4.0 | 0.84% | 4.0 | 100.0% | 0.0 | 0.0% | 0.0 | 0.0% |
| iC4 | 25.0 | 25.0% | 357.1 | 75.0% | 357.1 | 75.04% | 0.0 | 0.0% | 35.7 | 40.0% | 10.7 | 40.0% |
| nC4 | 12.0 | 12.0% | 21.4 | 4.5% | 21.4 | 4.50% | 0.0 | 0.0% | 17.1 | 19.2% | 5.1 | 19.2% |
| i-C4= | 15.0 | 15.0% | 24.6 | 5.2% | 45.9 | 9.65% | 0.0 | 0.0% | 4.6 | 5.1% | 1.4 | 5.1% |

TABLE 1-continued

| | | | | | | | | | | | | |
|---|---|---|---|---|---|---|---|---|---|---|---|---|
| 1-C4= | 15.0 | 15.0% | 18.4 | 3.9% | 9.2 | 1.93% | 0.0 | 0.0% | 0.9 | 1.0% | 0.3 | 1.0% |
| t-2-C4= | 12.0 | 12.0% | 25.3 | 5.3% | 23.0 | 4.82% | 0.0 | 0.0% | 18.4 | 20.6% | 5.5 | 20.6% |
| c-2-C4= | 15.5 | 15.5% | 23.5 | 4.9% | 13.8 | 2.89% | 0.0 | 0.0% | 11.0 | 12.3% | 3.3 | 12.3% |
| 1,3C4== | 0.5 | 0.5% | 0.5 | 0.1% | 0.0 | 0.00% | 0.0 | 0.0% | 0.0 | 0.0% | 0.0 | 0.0% |
| C5 | 1.0 | 1.0% | 1.0 | 0.2% | 1.0 | 0.21% | 0.0 | 0.0% | 1.0 | 1.1% | 0.3 | 1.1% |
| DIM | 0.0 | 0.0% | 0.0 | 0.0% | 0.5 | 0.11% | 0.0 | 0.0% | 0.5 | 0.6% | 0.1 | 0.6% |
| sum | 100.0 | 100.0% | 475.9 | 100.0% | 475.9 | 100.00% | 4.0 | 100.0% | 89.3 | 100.0% | 26.8 | 100.0% |

| | Stream | | | | | | | | | |
|---|---|---|---|---|---|---|---|---|---|---|
| | 310 | | 34 | | 35 | | 36 | | 311 | |
| C3 | 0.0 | 0.0% | 0.0 | 0.0% | 0.0 | 0.0% | 0.0 | 0.0% | 0.0 | 0.0% |
| iC4 | 25.0 | 40.0% | 321.4 | 84.0% | 321.4 | 84.0% | 0.0 | 0.0% | 332.1 | 88.4% |
| nC4 | 12.0 | 19.2% | 4.3 | 1.1% | 4.3 | 1.1% | 0.0 | 0.0% | 9.4 | 2.5% |
| i-C4= | 3.2 | 5.1% | 41.3 | 10.8% | 8.3 | 2.2% | 0.0 | 0.0% | 9.6 | 2.6% |
| 1-C4= | 0.6 | 1.0% | 8.3 | 2.2% | 3.1 | 0.8% | 0.0 | 0.0% | 3.4 | 0.9% |
| t-2-C4= | 12.9 | 20.6% | 4.6 | 1.2% | 7.8 | 2.0% | 0.0 | 0.0% | 13.3 | 3.5% |
| c-2-C4= | 7.7 | 12.3% | 2.8 | 0.7% | 4.7 | 1.2% | 0.0 | 0.0% | 8.0 | 2.1% |
| 1,3C4== | 0.0 | 0.0% | 0.0 | 0.0% | 0.0 | 0.0% | 0.0 | 0.0% | 0.0 | 0.0% |
| C5 | 0.7 | 1.1% | 0.0 | 0.0% | 0.0 | 0.0% | 0.3 | 0.9% | 0.0 | 0.0% |
| DIM | 0.3 | 0.6% | 0.0 | 0.0% | 33.1 | 8.6% | 33.2 | 99.1% | 0.0 | 0.0% |
| sum | 62.5 | 100.0% | 382.7 | 100.0% | 382.7 | 100.0% | 33.5 | 100.0% | 375.9 | 100.0% |

Example 2

The process for producing isoolefin dimers from a hydrocarbon flow containing $C_4$ hydrocarbons was simulated using a process configuration according to FIG. 4.

Example 2 presents system where skeletal isomerization and dimerization are connected in a simpler manner. The mixed $C_4$-feed 41 is connected with the recycle $C_4$-stream 49 and conducted to the skeletal isomerization unit A. The isomerized stream 43 is conducted to the dimerization unit B. The dimerized product is further conducted to the recycle column C. This column separates dimer product and the necessary amount of the unreacted $C_4$'s from the dimerization effluent as bottom product 45. The $C_4$ recycle stream is taken as side draw 49 and $C_3$s are removed from the recycle via the distillate of column C. The bottom product of column C, stream 45 is further divided in column D into dimer product 46 and C4 raffinate stream 47. The conversion to dimers can be optimized by adjusting the recycle stream 49. The advantage of this flow scheme compared to the previous one is that it is slightly simpler, but because $C_4$-splitting is not done before the dimerization unit, that has to handle the whole isomerization unit effluent. Efficient heat integration between skeletal isomerization unit and e.g. the column C is easy to arrange here.

The amounts and percentages of each component in each flow are presented in Table 2

TABLE 2

| | Stream | | | | | | | | | | | |
|---|---|---|---|---|---|---|---|---|---|---|---|---|
| | 41 | | 42 | | 43 | | 44 | | 48 | | 49 | |
| C3 | 4.0 | 4.0% | 8.0 | 1.5% | 8.0 | 1.5% | 8.0 | 1.5% | 4.0 | 100.0% | 4.0 | 0.9% |
| iC4 | 25.0 | 25.0% | 416.7 | 79.2% | 416.7 | 79.3% | 416.7 | 79.3% | 0.0 | 0.0% | 391.7 | 92.0% |
| nC4 | 12.0 | 12.0% | 18.5 | 3.5% | 18.5 | 3.5% | 18.5 | 3.5% | 0.0 | 0.0% | 6.5 | 1.5% |
| i-C4= | 15.0 | 15.0% | 22.3 | 4.2% | 40.6 | 7.7% | 8.1 | 1.5% | 0.0 | 0.0% | 7.3 | 1.7% |
| 1-C4= | 15.0 | 15.0% | 22.3 | 4.2% | 8.1 | 1.5% | 8.1 | 1.5% | 0.0 | 0.0% | 7.3 | 1.7% |
| t-2-C4= | 12.0 | 12.0% | 18.1 | 3.4% | 20.3 | 3.9% | 20.3 | 3.9% | 0.0 | 0.0% | 6.1 | 1.4% |
| c-2-C4= | 15.5 | 15.5% | 18.5 | 3.5% | 12.2 | 2.3% | 12.2 | 2.3% | 0.0 | 0.0% | 3.0 | 0.7% |
| 1,3C4== | 0.5 | 0.5% | 0.5 | 0.1% | 0.0 | 0.0% | 0.0 | 0.0% | 0.0 | 0.0% | 0.0 | 0.0% |
| C5 | 1.0 | 1.0% | 1.0 | 0.2% | 1.0 | 0.2% | 1.0 | 0.2% | 0.0 | 0.0% | 0.0 | 0.0% |
| DIM | 0.0 | 0.0% | 0.0 | 0.0% | 0.0 | 0.0% | 32.5 | 6.2% | 0.0 | 0.0% | 0.0 | 0.0% |
| sum | 100.0 | 100.0% | 525.9 | 100.0% | 525.4 | 100.0% | 525.4 | 100.0% | 4.0 | 100.0% | 425.9 | 100.0% |

| | Stream | | | | | |
|---|---|---|---|---|---|---|
| | 45 | | 46 | | 47 | |
| C3 | 0.0 | 0.0% | 0.0 | 0.0% | 0.0 | 0.0% |
| iC4 | 25.0 | 26.2% | 0.0 | 0.0% | 25.0 | 40.3% |
| nC4 | 12.0 | 12.6% | 0.0 | 0.0% | 12.0 | 19.4% |
| i-C4= | 0.8 | 0.9% | 0.0 | 0.0% | 0.8 | 1.3% |
| 1-C4= | 0.8 | 0.9% | 0.0 | 0.0% | 0.8 | 1.3% |
| t-2-C4= | 14.2 | 14.9% | 0.0 | 0.0% | 14.2 | 22.9% |
| c-2-C4= | 9.1 | 9.6% | 0.0 | 0.0% | 9.1 | 14.7% |
| 1,3C4== | 0.0 | 0.0% | 0.0 | 0.0% | 0.0 | 0.0% |
| C5 | 1.0 | 1.0% | 1.0 | 3.0% | 0.0 | 0.0% |
| DIM | 32.5 | 34.0% | 32.5 | 97.0% | 0.0 | 0.0% |
| sum | 95.5 | 100.0% | 33.5 | 100.0% | 62.0 | 100.0% |

Example 3

The process for producing isooctane from a hydrocarbon flow containing isobutene was simulated using a process configuration according to FIG. 5.

Example 3 presents a system where the $C_4$ feed stream 51 is first conducted to the skeletal isomerization unit A. The effluent of isomerization is combined with the $C_4$ recycle stream 59 and the combined stream 53 is conducted to the dimerization unit B. The effluent of the dimerization unit 54 is conducted to the recycle column C. This column separates dimer product and the necessary amount of the unreacted $C_4$'s from the dimerization effluent as bottom product 55. The $C_4$ recycle stream is taken as side draw 59 and $C_3$'s are removed from the recycle via the distillate of column C. The bottom product of column C, stream 55 is further splitted in column D into dimer product 56 and $C_4$ raffinate stream 57. The advantage of this system is that the skeletal isomerization unit can be made essentially smaller that in the two previous cases because it needs only to handle the fresh $C_4$ feed stream. On the other hand, there are not similar possibilities to control the conversion to dimers as in the two previous cases.

TABLE 3

| | \multicolumn{12}{c|}{Stream} | | | | | | | | | | | |
|---|---|---|---|---|---|---|---|---|---|---|---|---|
| | 51 | | 52 | | 53 | | 54 | | 58 | | 59 | |
| C3 | 4.0 | 4.0% | 4.0 | 4.0% | 8.0 | 4.3% | 8.0 | 4.3% | 4.0 | 100.0% | 4.0 | 4.6% |
| iC4 | 25.0 | 25.0% | 25.0 | 25.0% | 83.3 | 44.4% | 83.3 | 44.4% | 0.0 | 0.0% | 58.3 | 66.6% |
| nC4 | 12.0 | 12.0% | 12.0 | 12.0% | 17.1 | 9.1% | 17.1 | 9.1% | 0.0 | 0.0% | 5.1 | 5.9% |
| i-C4= | 16.0 | 16.0% | 28.8 | 28.8% | 33.0 | 17.6% | 6.6 | 3.5% | 0.0 | 0.0% | 4.3 | 4.9% |
| 1-C4= | 16.0 | 16.0% | 5.8 | 5.8% | 11.5 | 6.2% | 8.9 | 4.8% | 0.0 | 0.0% | 5.8 | 6.6% |
| t-2-C4= | 11.0 | 11.0% | 14.4 | 14.4% | 21.1 | 11.2% | 22.3 | 11.9% | 0.0 | 0.0% | 6.7 | 7.6% |
| c-2-C4= | 14.5 | 14.5% | 8.6 | 8.6% | 12.0 | 6.4% | 13.4 | 7.1% | 0.0 | 0.0% | 3.3 | 3.8% |
| 1,3C4== | 0.5 | 0.5% | 0.0 | 0.0% | 0.0 | 0.0% | 0.0 | 0.0% | 0.0 | 0.0% | 0.0 | 0.0% |
| C5 | 1.0 | 1.0% | 1.0 | 1.0% | 1.0 | 0.5% | 1.0 | 0.5% | 0.0 | 0.0% | 0.0 | 0.0% |
| DIM | 0.0 | 0.0% | 0.5 | 0.5% | 0.5 | 0.3% | 26.9 | 14.4% | 0.0 | 0.0% | 0.0 | 0.0% |
| sum | 100.0 | 100.0% | 100.0 | 100.0% | 187.6 | 100.0% | 187.6 | 100.0% | 4.0 | 100.0% | 87.6 | 100.0% |

| | \multicolumn{6}{c|}{Stream} | | | | | |
|---|---|---|---|---|---|---|
| | 55 | | 56 | | 57 | |
| C3 | 0.0 | 0.0% | 0.0 | 0.0% | 0.0 | 0.0% |
| iC4 | 25.0 | 26.0% | 0.0 | 0.0% | 25.0 | 36.7% |
| nC4 | 12.0 | 12.5% | 0.0 | 0.0% | 12.0 | 17.6% |
| i-C4= | 2.3 | 2.4% | 0.0 | 0.0% | 2.3 | 3.4% |
| 1-C4= | 3.1 | 3.3% | 0.0 | 0.0% | 3.1 | 4.6% |
| t-2-C4= | 15.6 | 16.3% | 0.0 | 0.0% | 15.6 | 22.9% |
| c-2-C4= | 10.0 | 10.4% | 0.0 | 0.0% | 10.0 | 14.7% |
| 1,3C4== | 0.0 | 0.0% | 0.0 | 0.0% | 0.0 | 0.0% |
| C5 | 1.0 | 1.0% | 1.0 | 3.6% | 0.0 | 0.0% |
| DIM | 26.9 | 28.1% | 26.9 | 96.4% | 0.0 | 0.0% |
| sum | 96.0 | 100.0% | 27.9 | 100.0% | 68.1 | 100.0% |

The invention claimed is:

1. A process for dimerizing olefinic hydrocarbons, comprising:

feeding a fresh olefinic hydrocarbon feedstock to a first reaction zone;

contacting the olefinic feedstock with a first catalyst in order to produce hydrocarbons having a modified isomeric structure;

withdrawing a first effluent containing at least a part of the hydrocarbons having a modified isomeric structure comprising the product of double bond isomerization from the first reaction zone;

contacting the first effluent with a second catalyst in a second reaction zone under conditions allowing for selective dimerization of the hydrocarbons having a modified isomeric structure in order to produce a dimerized reaction product;

withdrawing a second effluent containing at least part of the dimerized reaction product from the second reaction zone; and conducting the second effluent to a separation zone, wherein the dimerized reaction product is separated from said second effluent.

2. The process according to clam 1, wherein the hydrocarbons having a modified isomeric structure comprise hydrocarbons having at least one alkyl side chain.

3. The process according to claim 1, wherein the hydrocarbons having a modified isomeric structure comprises a mixture of hydrocarbons having at least one alkyl side chain and products of double bond isomerization.

4. The process according to any one of the preceding claims, wherein the fresh olefinic feedstock comprises $C_3$-$C_{10}$ olefins.

5. The process according to claim 1, wherein the fresh olefinic feedstock is selected from the group of linear and branched $C_4$-olefins.

6. The process according to claim 1, wherein the fresh olefinic feed of the process comprises an olefinic feedstock essentially consisting of 1-butene, 2-butene, isobutene and mixtures thereof.

7. The process according to claim 1, wherein the dimerized reaction product is a strongly branched dimer of said olefins.

8. The process according to claim 1, wherein the dimerized reaction product is a codimer of said olefins.

9. The process according to claim 1, wherein at least 50% of the fresh olefin feed is dimerized in the second reaction zone.

10. The process according to claim 1, wherein the second reaction zone has a once-through conversion rate of at least 50%.

11. The process according to claim 1 wherein the dimerized reaction product is hydrogenated.

12. The process according to claim 1, wherein the light hydrocarbons remaining after isomerization are conducted to alkylation.

13. The process according to claim 1, wherein at least a part of the remaining light hydrocarbons is recycled to the first reaction zone.

14. The process according to claim 13, wherein at least 50 mole-% of the unreacted light hydrocarbons of the second effluent are recovered and recycled to the first reaction zone.

15. The process according to claim 13, wherein the molar rate of recycled light hydrocarbons to the fresh olefinic feedstock fed into the first reaction zone amounts to about 0.1 to 0.4, calculated on the basis of the $C_3$-$C_{10}$ olefins contained therein.

16. The process according to claim 1, wherein the first catalyst is an isomerization catalyst.

17. The process according to claim 1, wherein the first catalyst is a selected from the group of zeolites, SAPO, amorphous aluminum silicates and aluminum oxide catalysts.

18. The process according to claim 17, wherein the zeolite is selected from the group consisting of synthetic and natural zeolites containing about 0.1 to 5 wt-% aluminum.

19. The process according to claim 17, wherein the zeolite is selected from the group consisting of ZSM-22, ZSM-23, ferrierite and ion-exchanged zeolites prepared therefrom.

20. The process according to claim 1, wherein the second catalyst is an acid ion exchange resin.

21. The process according to claim 1, wherein the second catalyst is a zeolite catalyst.

22. The process according to claim 21, wherein the zeolite is selected from the group consisting of synthetic and natural zeolites containing about 0.1 to 5 wt-% aluminum.

23. The process according to claim 21, wherein the zeolite is selected from the group consisting of ZSM-5, ZSM-22, ZSM-23, ferrierite and ion-exchanged zeolites prepared therefrom.

24. The process according to claim 19, wherein the first effluent contacted with the second catalyst contains less than 0.1 mole-% polar compounds.

25. The process according to claim 1, wherein the reactions in the first and second reaction zones are carried out essentially in the absence of polar compounds.

26. The process according to claim 1, wherein the first and second reaction zones have a common regeneration zone.

27. The process according to claim 1, wherein the catalysts in the first and second reaction zones are of similar type.

28. A process for converting a fresh olefinic hydrocarbon feedstock, mainly containing linear and branched $C_{3-7}$ olefins, into a gasoline component containing dimerized components, comprising isomerizing the linear and branched olefins of the feedstock to produce $C_{3-7}$ olefins having a modified isomeric structure, and dimerizing the modified $C_{3-7}$ olefins to produce a dimerization product mainly comprising $C_6$-$C_{12}$ hydrocarbons.

29. The process according to claim 4, wherein the fresh olefmic feedstock comprises $C_3$-$C_7$ olefins.

30. The process according to claim 18 or 22, wherein said aluminum is contained in an amount of about 0.3 to 3 wt-%.

31. The process according to claim 18 or 22, wherein said aluminum is contained in an amount of about 0.5 to 2 wt-%.

* * * * *